(12) United States Patent
Jennewein et al.

(10) Patent No.: US 9,938,549 B2
(45) Date of Patent: Apr. 10, 2018

(54) PROCESS FOR PRODUCING MONOSACCHARIDES

(71) Applicant: Jennewein Biotechnologie GmbH, Rheinbreitbach (DE)

(72) Inventors: Stefan Jennewein, Bad Honnef (DE); Katja Parschat, Rheinbreitbach (DE)

(73) Assignee: Jennewein Biotechnologie GmbH, Rheinbreitbach (DE)

( * ) Notice: Subject to any disclaimer, the term of this patent is extended or adjusted under 35 U.S.C. 154(b) by 0 days.

(21) Appl. No.: 14/700,038

(22) Filed: Apr. 29, 2015

(65) Prior Publication Data

US 2015/0240277 A1  Aug. 27, 2015

Related U.S. Application Data

(63) Continuation of application No. PCT/EP2013/068579, filed on Sep. 9, 2013.

(30) Foreign Application Priority Data

Oct. 31, 2012 (EP) .................................... 12190801

(51) Int. Cl.
| | |
|---|---|
| C12P 19/02 | (2006.01) |
| C12P 19/18 | (2006.01) |
| C12N 9/10 | (2006.01) |
| C12N 9/24 | (2006.01) |

(52) U.S. Cl.
CPC ............ C12P 19/02 (2013.01); C12N 9/1051 (2013.01); C12N 9/2402 (2013.01); C12P 19/18 (2013.01)

(58) Field of Classification Search
None
See application file for complete search history.

(56) References Cited

U.S. PATENT DOCUMENTS

2009/0082307 A1   3/2009  Samain et al.

FOREIGN PATENT DOCUMENTS

| EP | 2 479 263 A1 | 7/2015 |
|---|---|---|
| JP | 2003-504072 A | 2/2003 |
| WO | WO 2005/055944 A2 | 6/2005 |
| WO | WO 2005/055944 A3 | 6/2005 |
| WO | WO 2010/070104 A1 | 6/2010 |
| WO | WO 2010/101158 A1 | 9/2010 |
| WO | WO 2012/112777 A2 | 8/2011 |
| WO | WO 2012/112777 A3 | 8/2011 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Hsu et al., "Addition of Autotrophic Carbon Fixation Pathways to Increase the Theoretical Heterotrophic Yield of Acetate", The Fourth International Conference on Computational Systems Biology (ISB2010), Suzhou, China, Sep. 9-11, 2010, pp. 314-322.*
Singh et al. Curr Protein Pept Sci. 2017, 18, 1-11.*
Kizer et al. Appl Environ Microbiol. May 2008;74(10):3229-41.*
Prather et al. Curr Opin Biotechnol. Oct. 2008;19(5):468-74.*
Ashida et al., "Two distinct alpha-1-fucosidases from Bifidobacterium bifidum are essential for the utilization of fucosylated milk oligosaccharides and glycoconjugates," *Glycobiology* 19(9):1010-1017 (Sep. 9, 2009, advance access publication on Jun. 11, 2009).
Baumgartner et al., "Construction of *Escherichia coli* strains with chromosomally integrated expression cassettes for the synthesis of 2'-fucosyllac," *Microbial Cell Factories* 12(40):1-13 (May 1, 2013).
International Search Report from the parent PCT Application No. PCT/EP2013/068579 7 pages (dated Oct. 28, 2013).
Written Opinion from the parent PCT Application No. PCT/EP2013/068579 10 pages (dated Oct. 28, 2013).
Katayama et al., "Novel bifidobacterial glycosidases acting on sugar chains of mucin glycoproteins," *Journal of Bioscience and Bioengineering* 99(5): 457-465 (2005).

\* cited by examiner

*Primary Examiner* — Christian Fronda
(74) *Attorney, Agent, or Firm* — Klarquist Sparkman, LLP

(57) ABSTRACT

The present invention relates to a process for producing a monosaccharide using a microorganism. The microorganism possesses a glycosyltransferase and a glycosidase which work together to synthesize a desired monosaccharide in free form by using an endogenous provided nucleotide activated monosaccharide, glycosylate a suitable acceptor substrate and release the desired monosaccharide by a hydrolysis reaction. The required acceptor substrate for the reaction is recycled and only needed in catalytic amounts. The monosaccharide is produced in free from and is retrieved from the supernatant of the cultivated microorganism.

12 Claims, 9 Drawing Sheets

| primer | Sequence (5' - 3') |
|---|---|
| 605 | TTACTCAGCAATAAACTGATATTCCGTCAGGCTGG (SEQ ID NO. 1) |
| 606 | TTGATAATCTCGCGCTCTTCAGCAGTCAGACTTTCCATATAGAGCGTAATTTCCG TTAACGTCGGTAGTGCTGACCTTGCCGGAGG (SEQ ID NO. 2) |
| 1119 | CTGTCTCTTATACACATCTCCTGAAATTGGCCAGATGATTAATTCCTAATTTTTGTT G (SEQ ID NO. 3) |
| 1120 | CTGTCTCTTATACACATCTCAGCATTACACGTCTTGAGCGATTGTGTAGG (SEQ ID NO. 4) |

Fig. 2

PROCESS FOR PRODUCING MONOSACCHARIDES

CROSS REFERENCE TO RELATED APPLICATIONS

This application is a continuation of international patent application PCT/EP2013/068579, filed on Sep. 9, 2013, designating the U.S., which international patent application has been published in English language and claims priority from European patent application 12 190 801.6, filed on Oct. 31, 2012. The entire contents of these priority applications are incorporated herein by reference.

BACKGROUND OF THE INVENTION

The present invention relates to process for producing monosaccharides, in particular for producing L-fucose or other scarce monosaccharides e.g. N-acetyl neuraminic acid, whereby a microorganism is used in the production process.

Carbohydrates are necessary in all forms of life by taking on vital functions in energy storage, structural function, signalling, information storage etc. For this task nature synthesizes several major monosaccharides like glucose, mannose, fructose, fucose, ribose, sialic acid, etc. and several minor ones for more specialized applications, like for example D-allose.

Whereas some monosaccharides can be obtained from nature in large amounts and at reasonable cost (e.g. glucose and fructose), most monosacccharides are rather scarce and can be found in nature only in small amounts, like for example L-fucose (6-deoxy-L-galactose).

For commercial production of monosaccharides, almost exclusively oligosaccharides obtained from nature are used as sources. These oligosaccharides are acid hydrolyzed and from the released monosaccharides the individual sugars are purified. Due to the high chemical similarity of the monosaccharides (mostly differing from each other only by the orientation of individual hydroxyl-groups) the separation of individual monosaccharides in pure form is rather laborious and costly.

L-fucose represents such a rare sugar, which is currently obtained via the hydrolysis of complex oligosaccharides, either from algae or bacterial origin. For the purification of individual monosaccharides from complex hydrolysates often noxious chemicals have to be employed, like for example lead acetate and excessive amounts of organic solvents. Therefore, the isolation of individual monosaccharides from a complex hydrolysate of oligosaccharides is challenging (due to the high chemical similarity of the individual monosaccharides released) and environmentally harmful (due to the excessive use of toxic chemicals, such a lead carbonate). Also the availability of oligosaccharides rich in a certain sugar can be rather restricted in nature and also highly variable due to seasonal changes. L-Fucose represents such a scare monosaccharide which is traditionally obtained by the acid hydrolysis of fucose-containing polysaccharides. Fucose is mainly derived from the polysaccharide fucoidan, a fucan monosulfate present in all common brown seaweeds comprising the families Fucaceae and Laminariaceae. Today, L-fucose is obtained in large quantities manly by the collection of brown seaweed belonging to the family Fucaceae, which can be found world-wide but in high amounts at the European shores of the Atlantic Ocean. The large-scale harvest of brown seaweed from sea shores causes environmental concerns and is limited by certain environmental protection laws.

For example, JP 2000351790 discloses a method for extracting fucoidan and for obtaining and separating a fucose-containing oligosaccharide from the extracted fucoidan.

Besides the hydrolysis of fucoidan from brown-seaweed recently a patent publication showed that L-fucose can also be obtained via the hydrolysis of natural occurring L-fucose containing bacterial polysaccharides: WO 2012/034996 A1 discloses a strain belonging to the Enterobacteriaceae family, which strain is able to produce extracellular polysaccharides which contain L-fucose. For the production of L-fucose, the polysaccharides produced by the strain are recovered and subjected to hydrolysis, e.g. by treatment with sulphuric acid or hydrochloric acid.

Besides the extraction of L-fucose from poly- or oligosaccharide hydrolysates, several synthetic routes for L-fucose have been developed starting from other monosaccharides, like L-arabinose, D-galactose, L-rhamnose, D-mannose and D-glucose. Generally the yields of these chemical syntheses are often rather poor and involve several steps. Besides involving several synthetic steps, extensive protection group chemistry has to be used for the chemical synthesis of L-fucose. In general, the large-scale chemical synthesis of monosaccharides have not proved economical viable in comparison to extraction from nature.

Thus, currently, the preparation of any monosaccharide in pure form requires a significant effort in the purification of other monosaccharides away from the target monosaccharide, often involving large volumes of organic solvents and other noxious chemicals. As a consequence, the exclusive accumulation of a single desired monosaccharide like for example L-fucose would be of immense help. Most microorganisms are restricted in the kinds of monosaccharides they are able to utilize. In addition, they often exert strong preferences towards certain monosaccharides in case that several monosaccharides are available at the same time as carbon source.

SUMMARY OF THE INVENTION

In view of the above, it is an object of the present invention to provide a new process for the production of a single desired monosaccharide in free form, by means of which the monosaccharide can be retrieved fast and efficiently, i.e. in large scale and cost-effectively and without negative environmentally effects.

This and other objects are achieved by a process for producing a monosaccharide, i.e. in large scale, in free form using a microorganism, the process comprising the steps of:

a) providing a microorganism possessing the following enzymatic activities for the synthesis of the monosaccharide: i) a glycosyltransferase specifically able to transfer, from an activated nucleotide monosaccharide, the monosaccharide to an acceptor-substrate to form an acceptor-monosaccharide-substrate, and ii) a glycosidase able to release the monosaccharide from the acceptor-substrate; wherein the microorganism is unable to metabolize the monosaccharide;

b) cultivating the microorganism in a medium suitable for growing the microorganism, whereby the monosaccharide is produced in a free form, c) recovering the free monosaccharide from the medium.

Further, this object is solved by a microorganism, preferably a recombinant host microorganism, and its use in the production of a monosaccharide in free form, the microorganism containing i) a glycosyltransferase specifically able to transfer, from an activated nucleotide monosaccharide, the monosaccharide to an acceptor-substrate to form an acceptor-monosaccharide-substrate, and ii) a glycosidase able to release the monosaccharide from the acceptor-substrate; wherein the microorganism is unable to metabolize the monosaccharide.

The object underlying the invention is completely solved in this way.

BRIEF DESCRIPTION OF THE DRAWINGS

Several embodiments of the invention are illustrated in the figures and explained in more detail in the following description. In the figures:

FIG. 2 a table listing the oligonucleotide primers used for generating DNA-fragments for generating the microorganism according to the invention;

FIG. 6 1H-NMR spectrum of the purified L-fucose obtained from the bacterial fermentation.

SEQUENCE LISTING

Figure 1A:
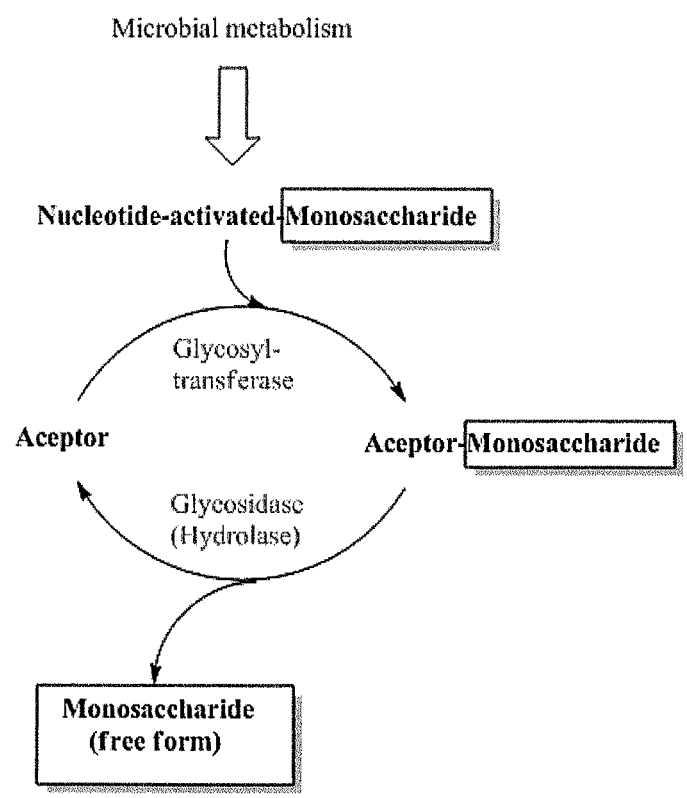
FIGS. 1A-1B show a schematic drawing of the pathway/process employed in the present invention (A) and the essential schematic part of the pathway for the exemplary production of L-fucose according to the invention (B)

The Sequence Listing is submitted as an ASCII text file [7291-94888-01_Sequence_Listing.txt, Apr. 28, 2015, 1.08 KB], which is incorporated by reference herein.

DETAILED DESCRIPTION OF SEVERAL EMBODIMENTS

Applicants' process has not previously been described, and utilizes a microorganism having two specific enzymatic activities, i.e. a glycosyltransferase and a glycosidase, wherein the glycosyltransferase is specifically able to transfer, from an activated nucleotide monosaccharide (which is either endogenously present or externally supplied), the monosaccharide to an acceptor-substrate so that an acceptor-monosaccharide-substrate is formed. In a subsequent step, the glycosidase releases the monosaccharide from the acceptor-substrate so that the free monosaccharide is provided.

Although unmodified microorganisms having the above described enzymatically features can be employed within the present invention, according to one aspect of the invention, the microorganism is a recombinant microorganism, wherein the recombinant microorganism has been transformed to comprise at least one of i) a nucleic acid sequence encoding a glycosyltransferase not naturally occurring in the microorganism, and/or ii) a nucleic acid sequence encoding a glycosidase not naturally occurring in said microorganism.

In other words, the recombinant microorganism can be transformed to either comprise a nucleic acid sequence encoding a glycosyltransferase not naturally occurring in the microorganism, or a nucleic acid sequence encoding a glycosidase not naturally occurring in said microorganism, or it can be transformed to comprise both, i.e. a nucleic acid sequence encoding a glycosyltransferase not naturally occurring in the microorganism, and a nucleic acid sequence encoding a glycosidase not naturally occurring in said microorganism.

With the newly provided process and the newly provided microorganism—recombinant or not—, it is—for the first time—possible to produce a desired monosaccharide in a free form and in large amounts, without necessitating chemicals or elaborate process steps. The process according to the invention represents a microbial fermentation process, suitable for getting employed for industrial large scale production of rare or other monosaccharides, which can be readily retrieved from the medium the microorganism is cultivated in.

By using a microorganism according to the invention, i.e. one that is expressing the glycosyltransferase, efficient fucosylation of an endogenous or externally supplied acceptor-substrate can be effected, and by the simultaneous expression of a glycosidase an unprecedented accumulation of large amounts of the free monosaccharide in the medium can be produced. In the presence of an acceptor substrate the glycosyltransferase and glycosidase are thus working synergistically together in the synthesis of free monosaccharide requiring only a catalytic amount of suitable acceptor. Thus the supplied acceptor substrate is fucosylated by the glycosyltransferase and the generated glycosylated product is recycled by the action of the glycosidase accepting the glycosylated product of the glycosyltransferase reaction.

The expression "monosaccharide" as used herein and as generally understood in the field of the invention, refers to the most basic unit of carbohydrates. Monosaccharides are the simplest form of sugar and are usually colourless, water-soluble, crystalline solids. Examples of monosaccharides include glucose, fructose, galactose, xylose, and ribose. Monosaccharides are the building blocks of disaccharides such as sucrose and polysaccharides such as cellulose and starch. "Oligosaccharide" as the term is used herein and as generally understood in the state of the art, refers to a saccharide polymer containing two monosaccharides or more.

The term "nucleic acid sequence encoding . . . " generally refers to any polyribonucleotide or polydeoxyribonucleotide, which may be unmodified RNA or DNA or modified RNA or DNA, and generally represents a gene which encodes a certain polypeptide or protein. The term includes, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. The term also encompasses polynucleotides that include a single continuous region or discontinuous regions encoding the polypeptide (for example, interrupted by integrated phage or an insertion sequence or editing) together with additional regions that also may contain coding and/or non-coding sequences.

In this context, the term "polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may contain amino acids other than the 20 gene encoded amino acids. "Polypeptide(s)" include those modified either by natural processes, such as processing and other post-translational modifications, but also by chemical modification techniques. It will be appreciated that the same type of modification may be present in the same or varying degree at several sites in a given polypeptide, without essentially altering the activity of the polypeptide. Also, a given polypeptide may contain many types of modifications. Modifications can occur anywhere in a polypeptide, including the peptide backbone, the amino acid side-chains, and the amino or carboxyl termini.

Presently, and throughout the present invention, the term "glycosyltransferase" designates and encompasses enzymes that are responsible for the biosynthesis of disaccharides, oligosaccharides and polysaccharides, and they catalyse the transfer of monosaccharide moieties from an activated nucleotide monosaccharide/sugar (the "glycosyl donor") to a glycosyl acceptor molecule.

According to one aspect of the invention, it is particularly preferred if the glycosyltransferase is a bacterial fucosyl-transferase, and preferably the alpha-1,2-fucosyltransferase encoded by the wbgL gene of E. coli:O126 (genebank acc. No. ADN43847).

Accordingly, the terms "alpha-1,2-fucosyltransferase" or "fucosyltransferase" or a nucleic acid/polynucleotide encoding an "alpha-1,2-fucosyltranferase" or "fucosyltransferase" refer to a glycosyltransferase that catalyzes the transfer of fucose from a donor substrate, for example, GDP-fucose, to an acceptor molecule in an alpha-1,2-linkage. The acceptor molecule can be a carbohydrate, an oligosaccharide, a protein or glycoprotein, or a lipid or glycolipid, and can be, e.g., N-acetylglucosamine, N-acetyllactosamine, galactose, fucose, sialic acid, glucose, lactose or any combination thereof.

"A glycosidase" or "a glycosidase able to release the monosaccharide from the acceptor-substrate" as used throughout the present invention and as it is understood in the relevant field, comprises any glycoside (or glycosyl) hydrolase that catalyzes the hydrolysis of glycosidic bonds to release smaller sugars, such as monosaccharides.

According to one aspect of the invention, it is particularly preferred if the glycosidase is a bacterial glycosidase, preferably a bacterial α-L-fucosidase. According to one embodiment of the invention, the 1,2-α-L-fucosidase gene afcA from Bifidobacterium bifidum (genebank accession no.: AY303700), codon optimized for the expression in E. coli, is used.

Within the scope of the present invention, also nucleic acid/polynucleotide and polypeptide polymorphic variants, alleles, mutants, functionally equivalent fragments, and interspecies homologs of the glycosyltransferases and glycosidases that are mentioned throughout the invention are comprised by those terms, in particular those that have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 25, 50, 100, 200, 500, 1000, or more amino acids, in particular, and e.g., to the amino acid sequence of the alpha-1,2-fucosyltransferase encoded by the wbgL gene of E. coli:O126 (acc. No. ADN43847) or to the amino acid sequence of the 1,2-α-L-fucosidase gene afcA from Bifidobacterium bifidum. The person skilled in the art will readily recognize upon reading the invention that any other glycosyltransferase or glycosidase can be employed, as long as these enzymes fulfil their enzymatic activities in the microorganism. Eventually, the sequences of the the glycosyltransferase and/or the glycosidase will have to be codon optimized with respect of the microorganism they are to be introduced in.

Within the context of this invention, "functionally equivalent", as used herein, refers to a polypeptide capable of exhibiting a substantially similar in vivo activity as the alpha-1,2-fucosyltransferase gene product encoded by the alpha-1,2-fucosyltransferase gene sequence described above or of the fucosidase gene product as described above, as judged by any of a number of criteria, including but not limited to antigenicity, i.e., the ability to bind to an anti-alpha-1,2-fucosyltransferase or 1,2-α-L-fucosidase antibody, immunogenicity, i.e., the ability to generate an antibody which is capable of binding an alpha-1,2-fucosyltransferase or fucosidase protein or polypeptide, as well as enzymatic activity.

The glycosyltransferase polypeptide and/or the glycosidase polypeptide as mentioned throughout the invention may be produced by recombinant DNA technology using techniques well known in the art. Methods which are well known to those skilled in the art can be used to construct expression vectors containing, e.g., alpha-1,2-fucosyltransferase and/or 1,2-α-L-fucosidase, coding sequences and appropriate transcriptional translational control signals. These methods include, for example, in vitro recombinant DNA techniques, synthetic techniques, and in vivo genetic recombination. See, for example, the techniques described in Sambrook et al., Molecular Cloning: A Laboratory Manual, 2nd Ed., Cold Spring Harbor Laboratory Press, Cold Spring Harbor, N.Y. (1989).

Presently, and throughout the invention, "recombinant" means genetically engineered DNA prepared by transplanting or splicing genes from one species into the cells of a host microorganism of a different species. Such DNA becomes part of the host's genetic makeup and is replicated.

"Microorganism" presently designates and encompasses any microscopic organism that comprises either a single cell, cell clusters, or multicellular relatively complex organisms, which is suitable to be employed in the process according to the invention, and particularly includes bacteria and yeast. A microorganism as employed according to the invention can be cultivated in a liquid medium, and generally needs a carbon source in the medium to grow and replicate.

Consequently, "a recombinant host microorganism" is designated to mean any microorganism containing, a nucleic acid sequences coding for a glycosyltransferase or a glycosidase, or coding for a glycosyltransferase and a glycosidase, wherein the nucleic acid sequences coding for these enzymes are nucleic acid sequences foreign to/not naturally occurring in the recombinant (host) cell and wherein the foreign/not naturally in said microorganism occurring sequence is integrated in the genome of the host microorganism cell. Thereby, "not naturally occurring" means that the nucleic acid sequence is foreign to said host microorganism cell, i.e. the nucleic acid sequences are heterologous with respect to the microorganism host cell. The heterologous sequence may be stably introduced, e.g. by transfection, transformation, or transduction, into the genome of the host microorganism cell, wherein techniques may be applied which will depend on the host cell the sequence is to be introduced. Various techniques are known to a person skilled in the art and are, e.g., disclosed in Sambrook et al., 1989, supra. Thus, the host cell the heterologous sequence has been introduced in, will produce the heterologous proteins the nucleic acid sequences according to the invention are coding for.

For recombinant production, host cells can be genetically engineered to incorporate expression systems or portions thereof and the nucleic acid sequences of the invention. Introduction of a nucleic acid sequence into the host microorganism cell can be effected by methods described in many standard laboratory manuals, such as Davis et al., Basic Methods in Molecular Biology, (1986), and Sambrook et al., 1989, supra.

Thus, the nucleic acid sequences according to the invention, may, e.g., be comprised in a vector which is to be stably transformed/transfected or otherwise introduced into host microorganism cells.

A great variety of expression systems can be used to produce the polypeptides of the invention. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses, and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and to synthesise a polypeptide in a host may be used for expression in this regard. The appropriate DNA sequence may be inserted into the expression system by any of a variety of well-known and routine techniques, such as, for example, those set forth in Sambrook et al., supra.

As used herein, the term "recovering" means isolating, harvesting, purifying, collecting or otherwise separating from the microorganism culture the monosaccharide produced by the microorganism according to the invention.

Throughout the invention, it is particularly preferred if the free monosaccharide to be produced is L-fucose or a neuraminic acid.

L-fucose is a hexose deoxy sugar and is—besides other fucosyltated oligosaccharides—found to be of major interest for chemical, pharmaceutical, cosmetic and nutritional appliances. Besides of its use for the production of fucosylated derivatives which are known for their antiallergic and emulsifying properties, L-fucose is also a common component of human milk oligosaccharides (HMO's), such as 2'-fucosyl-lactose.

According to a preferred embodiment, the acceptor-substrate is either endogenous to said microorganism or is added to the medium the microorganism is cultivated in. An endogenous acceptor-substrate can be, e.g., any disaccharide or monosaccharide, a glycosylated protein or a lipopolysaccharide present in the microorganism.

According to one aspect of the invention, the acceptor-substrate is added externally to said microorganism or to the microorganism cultured in a medium, and preferably lactose or lactulose is added.

In a preferred embodiment, the microorganism is cultivated in a medium containing a carbon source that is selected from glycerol, sucrose, glucose, fructose, molasses, lactose, xylose, cellulose, syngas or carbon monoxide. In this context it is to be understood that any other—preferably low-cost—fermentation substrates can be employed as carbon source, and the person skilled in the art will readily able to employ a carbon source suitable within the present invention in order to grow the microorganism to produce the desired monosaccharide in a large scale.

According to one aspect of the invention, the process is a batch or a continuous fermentation process.

Thus, according to one aspect of the invention, i.e. in a continuous process, a carbon source is constantly added to the medium during the cultivating step of the microorganism, e.g. a recombinant microorganism By constantly adding the carbon source during the cultivation step, a constant and effective production of the monosaccharide is accomplished.

According to another aspect, i.e. in a batch process, the process does not include steps of externally adding substances during the fermentation process.

According to another aspect of the invention, the monosaccharide is recovered from supernatant of the cultivated recombinant host microorganism, which supernatant is obtained by centrifuging the cultivated host microorganism to obtain a supernatant and a host microorganism pellet.

With the newly provided process, it is possible to retrieve the produced monosaccharide from the medium the host microorganism is cultivated in, since the monosaccharide which is produced in a microorganism cell is transported into the medium, thus making it effortlessly possible to recover the monosaccharide from the supernatant, once the cells of the microorganism have been separated from the cultivation medium.

According to another preferred embodiment of the process according to the invention, prior to isolating the monosaccharide in step c), a beta-galactosidase is added to medium the host microorganism is cultivated in and/or endogenous production of a beta-galactosidase is induced in the microorganism.

By means of this feature it can be achieved that other monosaccharides—besides the desired monosaccharide—, which other monosaccharides are produced in the microorganism during the synthesis of the desired monosaccharide, and which other monosaccharides interfere with the purification step of the desired monosaccharide, can be metabolised, so that the recovering step of the desired monosaccharide is further improved and facilitated. According to the invention, this can be achieved by either inducing an otherwise deregulated beta-galactosidase towards the end of the process; this means that during synthesis of the desired monosaccharide, the beta-galacosidase is deregulated and may be induced, e.g. by temperature or adding a inductor, e.g. tetracyclin, at the end of the fermentation process. Alternatively or in addition, the enzyme beta-galactosidase (or any other oligo- or monosaccharide metabolising enzyme(s)) may be externally added to the medium at the end of the process according to the invention, which is particularly preferred when the endogenous gene encoding beta-galactosidase has been inactivated or deleted. In doing so, undesired oligo- and or monosaccarides cannot accumulate and do not interfere with the recovering of the desired monosaccharide. In this context, it is to be understood that, besides beta-galactosidase, also other metabolic enzymes can be either regulated in the mentioned way in the microorganism in order to metabolize otherwise interfering undesired oligo- and monosaccharides, and one skilled in the art will—upon reading the invention—readily recognize other suitable pathways or enzymes to regulate/activate or supply, which will depend from the acceptor to be degraded.

"Beta-galactosidase" as it is used herein and as generally understood within the field of the invention, is a hydrolase enzyme that catalyzes the hydrolysis of beta-galactosides into monosaccharides.

"Regulated" within the present context with reference to a gene is generally understood as a gene, whose expression can be regulated in a controlled fashion, e.g. down- or up-regulated, i.e. the quantity of the synthesised protein encoded by the regulated gene is different, e.g. de-/down-regulated or upregulated, from the otherwise unregulated gene.

By adding the enzyme beta-galactosidase to the medium and/or the supernatant, the acceptor-substrate still present in the medium can be cleaved—in case where lactulose is used: the lactulose glycosidic bond is cleaved and galactose and fructose are released—and the resulting monosaccharides can be effectively metabolized by the used *E. coli* strain. Thus, the supplied disaccharide, preferably lactulose or lactose, can be efficiently removed from the culture medium. In this case, the beta-galactosidase which is eventually naturally present in the microorganism, e.g. such as *Escherichia coli*, can be inactivated through a gene knockout, or similar gen inactivation Also, according to another aspect of the invention, prior to recovering the monosaccharide from the supernatant, the supernatant is treated with beta-galactosidase and then contacted with the cultivated host microorganisms.

According to one aspect of the invention, the process according to the invention comprises the following steps:
  a) providing, in a medium suitable for growing a microorganism, a recombinant host microorganism which has been transformed to comprise a) a nucleic acid sequence encoding a glycosyltransferase not naturally occurring in the microorganism, and/or b) a nucleic acid sequence encoding a glycosidase not naturally occurring in said microorganism, wherein the microorganism is unable to metabolize the monosaccharide to be produced,
  b) adding an acceptor-substrate to the medium the host microorganism is cultivated in, wherein the acceptor-substrate is a disaccharide, preferably lactose or lactulose,
  c) cultivating the recombinant host microorganism in said medium whereby the monosaccharide is produced in a free form,
  d) recovering the free monosaccharide from the medium.

As mentioned above, and as already described in connection with the process according to the invention, the invention also relates to a recombinant host microorganism that is transformed to be able to grow on a sole carbon source and to contain a) a nucleic acid sequence encoding a glycosyltransferase polypeptide not naturally occurring in said host microorganism, and b) a nucleic acid sequence encoding a glycosidase polypeptide not naturally occurring in said microorganism.

The definitions used and set forth above for specific terms in connection with the process do also apply for the recombinant microorganism presented therein.

According to a preferred embodiment, the microorganism—used in the process according to the invention and claimed therein—is selected from a bacterium or a yeast, and more preferably, the host microorganism is an *Escherichia coli* strain or a *Saccharomyces* sp. strain.

The bacterium *Escherichia coli* and the yeast *Saccharomyces* sp. have the advantage that these microorganisms can be grown easily and inexpensively in laboratory settings, and the bacterium and yeast have been intensively investigated for over 60 years.

Accordingly, in a preferred embodiment, the host microorganism used in the process according to the invention and otherwise claimed therein is selected from the group consisting of bacteria and yeast, and is preferably an *Escherichia coli* strain.

It is further preferred in an embodiment of the present invention, if the recombinant host microorganism is further transformed to either lack a gene encoding beta-galactosidase—or comprise a deregulated beta-galactosidase encoding gene-, and L-fucose isomerase, L-fuculose kinase, and UDP-glucose:undecaprenyl phosphate glucose-1-phosphate transferase.

This embodiment has the advantage that intracellular degradation of the produced monosaccharide L-fucose and production of colonic acid is prevented and in the case of the beta-galctosidase the acceptor molecule is not degraded.

In another preferred embodiment, the recombinant host microorganism is further transformed to contain genes enabling the recombinant host microorganism to grow on sucrose or glycerol as sole carbon source, and it is particularly preferred if the csc-gene cluster of *Escherichia coli* W (acc. No. CP0021851) is integrated into the genome of the host microorganism, which gene cluster comprises the genes sucrose permase, fructokinase, sucrose hydrolase, and a transcriptional repressor (genes cscB, cscK, cscA, and cscR, respectively), that enable the transformed microorganism to grow on sucrose as sole carbon source.

According to a preferred embodiment of the process or the microorganism of the invention, and as mentioned above, the nucleic acid encoding a glycosyltransferase polypeptide is a 2-fucosyltransferase, and a 1,2-alpha-L-fucosidase. For the definition of this enzyme, see above.

In this connection it is noted that the embodiments listed as preferred for the process according to the invention all do apply for the claimed microorganism, where applicable.

Accordingly, the present invention also relates to the use of a microorganism possessing the following enzymatic activities for the synthesis of the monosaccharide: i) a glycosyltransferase specifically able to transfer, from an activated nucleotide monosaccharide substrate, the monosaccharide to an acceptor to form an acceptor-monosaccharide substrate, and ii) a glycosidase able to release the monosaccharide from the acceptor; wherein the microorganism is unable to metabolize the monosaccharide, and the invention further relates to the use of the recombinant microorganism according to the invention for the production of a monosaccharide, in particular of L-fucose.

It is noted that the definitions set forth above for describing certain terms of the process according to the invention shall apply for the microorganism, recombinant or unmodified, as claimed and described herein.

Alternatively, the method for producing monosaccharides may be applied on cell-free systems, whereby the enzymes according to the invention, the acceptor substrate(s), and, as the case may be, other reaction mixture ingredients, including other glycosyltransferases and accessory enzymes are combined by admixture in an aqueous reaction medium. The enzymes can be utilized free in solution, or they can be bound or immobilized to a support such as a polymer and the substrates may be added to the support. The support may be, e.g., packed in a column.

In particular, the present invention relates to a process wherein a recombinant *Escherichia coli* strain is used as recombinant host microorganism, wherein in the recombinant *Escherichia coli* strain the L-fucose isomerase gene and L-fuculose kinase gene have been deleted, and wherein the recombinant *Escherichia coli* strain has been transformed to comprise a) genes enabling the *E. coli* strain to grow on sucrose or glycerol as sole carbon source, the genes encoding, respectively, sucrose permase, fructokinase, sucrose hydrolase, and a transcriptional repressor, b) a gene encoding a 2-fucosyltransferase, and c) a gene encoding a 1,2-alpha-fucosidase.

Further advantages follow from the description of the embodiments and the attached drawings.

It goes without saying that the abovementioned features and the features which are still to be explained below can be used not only in the respectively specified combinations, but also in other combinations or on their own, without departing from the scope of the present invention.

EXAMPLES

As schematically shown in FIG. 1A, the process according to the invention—and the microorganism used in the process—utilises a nucleotide-activated monosaccharide present in the microorganism, and transfers—via the enzymatic activity of the glycosyltransferase—the monosaccharide moiety to an acceptor—which may be endogenously present in the microorganism and/or externally supplied—to form an acceptor-monosaccharide-substrate or complex. By enzymatic activity of the glycosidase (hydrolase), the monosaccharide is released from the acceptor-monosaccharide-substrate and can be retrieved in free form (see FIG. 1A).

Figure 1B:
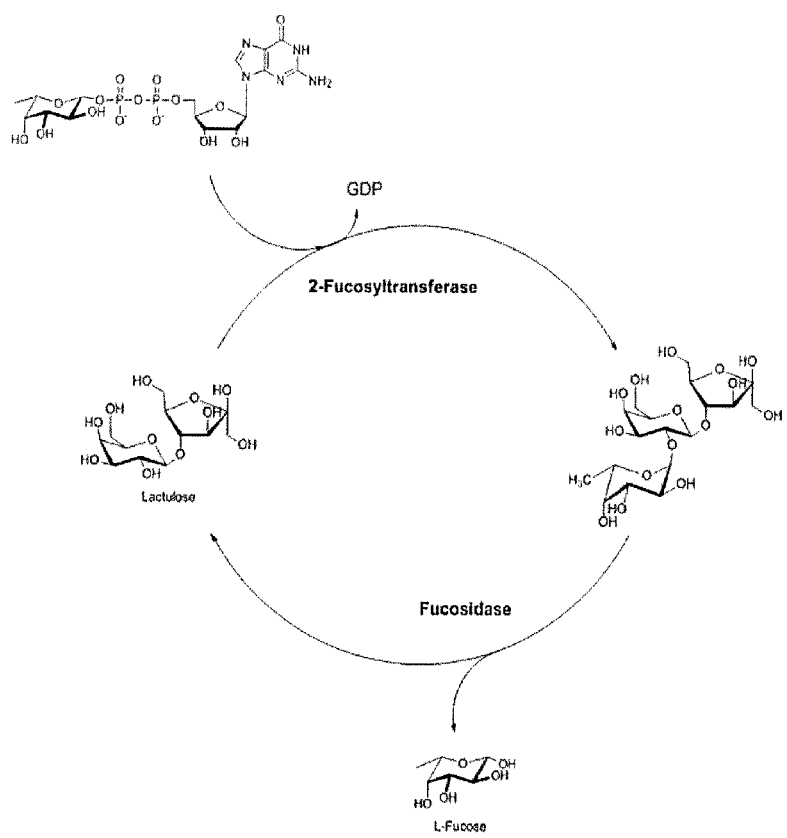

As an exemplary monosaccharide, L-Fucose was produced from sucrose or from glycerol in a recombinant *Escherichia coli* strain. FIG. 1B shows a portion of the schematic pathway for the production of L-fucose. In the microorganism, GDP-fucose was synthesized via the de novo pathway and lactulose served as exemplary acceptor substrate in a 2-fucosyltransferase catalyzed reaction. Hydrolysis of the glycosidic linkage by a 1,2-α-L-fucosidase releases L-fucose (see FIG. 1B).

Development of the *E. coli* L-Fucose Production Strain

First lacZ was inactivated in *E. coli* BL21(DE3) (Novagen) (see FIG. 2A table 1) by mutagenesis using mismatch-oligonucleotides as described by Ellis et al., 2001. The gal-operon (galETKM) was amplified from *E. coli* K12 TG1 using primers 605 and 606 (all primers used are listed in table 2 of FIG. 2B) and inserted into the galM ybhJ locus of *E. coli* BL21(DE3) lacZ by homologous recombination facilitated by using the red recombinase helper plasmid pKD46 (Datsenko and Warner, "*One-step inactivation of chromosomal genes in Escherichia coli K-12 using PCR products*", Proc. Natl. Acad. Sci. USA 97:6640-6645 (2000)). Next, araA was inactivated by oligonucleotide mutagenesis. In strain *E. coli* BL21(DE3) lacZ Gal$^+$ araA the gene wcaJ was deleted. Genomic deletions were performed according to the method of Datsenko and Warner ((2000), see above). WcaJ probably encodes a UDP-glucose:undecaprenyl phosphate glucose-1-phosphate transferase catalyzing the first step in colanic acid synthesis (Stevenson et al., "*Organization of the Escherichia coli K-12 gene cluster responsible for production of the extracellular polysaccharide colonic acid*", J. Bacteriol. 178:4885-4893; (1996)); production of colanic acid would compete for GDP-fucose with the fucosyltransferase reaction. To prevent intracelluar degradation of L-fucose, genes encoding L-fucose isomerase (fucI) and L-fuculose kinase (fucK) had been deleted from the genome of *E. coli* strain BL21 (DE3) lacZ Gal$^+$ araA ΔwcaJ.

Using plasmid pINT2-lacY-aadA (appendix sequence 1) as template, the lactose transporter gene lacY, originally from *E. coli* K12 TG1 (acc. no. ABN72583), together with the preceding promoter $P_{tet}$ and the FRT-site flanked streptomycine resistence gene was amplified with primers 1119 and 1120. The resulting PCR-product carried on both sites the 19-bp Mosaic End recognition sites for the EZ-Tn5 transposase. The EZ-Tn5<$P_{tet}$-lacY-FRT-aadA-FRT> transposon was used to produce an EZ-Tn5 transposome with EZ-Tn5™ transposase (Epicentre, USA), with which electrocompetent cells of *E. coli* BL21 (DE3) lacZ Gal$^+$ araA ΔwcaJ ΔfucI ΔfucK were transformed. The resistance gene was eliminated from streptomycine resistant clones by the FLP recombinase encoded on plasmid pCP20 (Datsenko and Warner, see above). The csc-gene cluster of *E. coli* W (acc. no. CP002185.1) comprises four genes for sucrose permase, fructokinase, sucrose hydrolase, and a transcriptional repressor (genes cscB, cscK, cscA, and cscR, respectively), that enable the strain to grow on sucrose as sole carbon source. This csc-cluster was integrated into the genome of the *E. coli* BL21(DE3) lacY-harbouring strain by transposition using plasmid pEcomar-cscABKR (appendix sequence 2). The csc-genes were flanked by the inverted terminal repeats specifically recognized by the mariner-like element Himar1 transposase (Bigot et al., "*Conservation of Palindromic and Mirror Motifs within Inverted Terminal Repeats of mariner-like Elements*", J. Mol. Biol. 351:108-116 (2005)) that is encoded on pEcomar and transcribed under the control of $P_{araB}$. For transposition mediated by the mariner transposase cells harbouring the respective plasmid were grown in 2'YT medium (Sambrook and Russel, 2001, Molecular Cloning: a laboratory manual) containing 100 µg/ml ampicillin and induced with 100 mM L-arabinose for at least 16 h at 30° C. Clones containing the transposon cassettes were selected on M9-agar (Sambrook and Russel, see above) plates containing 1% sucrose, in the case of insertion of the csc-cluster, or on 2'YT agar containing the respective antibiotic. *E. coli* BL21 (DE3)::($P_{tet}$-lacY)(cscBKAR) lacZ Gal$^+$ araA ΔwcaJ ΔfucI ΔfucK was able to grow on sucrose as sole carbon source. The 2-fucosyltransferase gene wbgL from *E. coli*: O126 (acc. no. ADN43847) was codon-optimized for expression in *E. coli* and prepared synthetically by GenScript Cooperation (USA). Using plasmid pINT2-wbgLco-neo (appendix sequence 3) as template, the wbgLco gene together with the preceding promoter $P_{tet}$ and the FRT-site flanked kanamycine resistance gene was amplified with primers 1119 and 1120; the resulting EZ-Tn5<$P_{tet}$-wbgLco-FRT-neo-FRT> transposon was integrated mediated by the EZ-Tn5™ transposase.

To enhance de novo synthesis of GDP-fucose, genes encoding phosphomannomutase (manB), mannose-1-phosphate guanosyltransferase (manC), GDPmannose-4,6-dehydratase (gmd), and GDP-L-fucose synthase (wcaG) from *E. coli* K12 DH5α were overexpressed in the *E. coli* BL21 (DE3) strain; the operon manCB is under control of $P_{tet}$, the operon gmd, wcaG is transcribed from the $P_{T5}$ promoter. The transposon cassette <$P_{tet}$-manCB-$P_{T5}$-gmd, wcaG-FRT-dhfr-FRT> was inserted from pEcomar C9-manCB-gmd, wcaG-dhfr (appendix sequence 4) mediated by the hyperactive C9-mutant of the mariner transposase Himar1 (Lampe et al., "*Hyperactive transposase mutants of the Himar1 mariner transposon*", Proc. Natl. Acad. Sci. USA 96:11428-11433 (1999)). Finally the 1,2-α-L-fucosidase gene afcA (codon optimizes for the expression in *E. coli* and synthezised by GeneScript Coorperation) from *Bifidobacterium bifidum* was inserted as <$P_{tet}$-afcAco-FRT-tet-FRT> transposon into the strain by transposition using pEcomarafcAco-tet (appendix sequence 5) and the mariner transposase.

Cultivation Conditions for L-Fucose Production

A: Using Sucrose as Carbon Source

*E. coli* BL21 (DE3) lacZ Gal$^+$ araA ΔwcaJ ΔfucI ΔfucK::($P_{tet}$-lacY)(cscBKAR)($P_{tet}$-wgbLco-neo)($P_{tet}$-manCB-$P_{T5}$- gmd, wcaG-dhfr)($P_{tet}$-afcAco-tet) was cultivated in a 3 L fermentor (New Brunswick, Edison, USA) starting with 800 mL mineral salts medium (Samain et al., "Production of O-acetylated and sulphated chitooligosaccharides by recombinant Escherichia coli strains harbouring different combinations of nod genes", J. Biotech. 72:33-47 (1999)) containing 3% sucrose as carbon source and the antibiotics tetracycline 7.5 µg/ml, kanamycine 15 µg/ml, and trimethoprim 10 µg/ml. Cultivation was started with a 2.5% (v/v) inoculum. Lactulose as acceptor in the fucosyltransferase reaction was added in several steps to an end-concentration of 33.75 mM. The culture was fed continuously with sucrose. Cells grew in about 66 h to an OD660 nm of 141 and produced 366 mM fucose (data not shown).

B: Using Glycerol as Carbon Source

E. coli BL21 (DE3) lacZ Gal⁺ araA ΔwcaJ ΔfucI ΔfucK::($P_{tet}$-lacY)(cscBKAR)($P_{tet}$-wgbLco-neo)($P_{tet}$-manCB-$P_{T5}$-gmd, wcaG-dhfr)($P_{tet}$-afcAco-tet) was cultivated in a 3 L fermentor (New Brunswick, Edison, USA) starting with 800 mL mineral salts medium (Samain et al., see above) containing 3% glycerol as carbon source and the antibiotics tetracycline 7.5 µg/ml, kanamycine 15 µg/ml, and trimethoprim 10 µg/ml. Cultivation was started with a 2.5% (v/v) inoculum. Lactulose as acceptor in the fucosyltransferase reaction was added in several steps to an end-concentration of 31.5 mM. The culture was fed continuously with glycerol. Cells grew in about 64 h to an OD660 nm of 212 and produced 78 mM fucose (data not shown).

Detection of L-Fucose

The supernatant of the growing cells was analysed by the thin layer chromatography TCL using silica gel TCL plates (Silica gel 60). A mixture of butanol:acetone:acetic acid:$H_2O$ (35/35/7/23 (v/v/v/v)) was used as mobile phase. For detection of the separated substances the TCL was soaked with Thymol reagent (0.5 g Thymol solved in 95 ml ethanol, 5 ml sulfuric acid added) and heated.

Analysis by high performance liquid chromatography was performed using a refractive index detector (RID-10A) (Shimadzu, Germany) and a Luna NH2 column (10 µm, 250 ' 4.6 mm) (Phenomenex, USA) connected to an HPLC system (Shimadzu, Germany). Elution was performed isocratically with acetonitril:$H_2O$ (80/20 (v/v)) as eluent at 35° C. and a flow rate of 3 ml/min. 20 µl of the sample were applied to the column. L-fucose concentration was calculated from a standard curve. Therefor 10% (v/v) 100 mM maltotriose were added to the HPLC samples as internal standard before they were filtered (0.22 µm pore size) and cleared by solid phase extraction on an ion exchange matrix (Strata ABW, Phenomenex).

L-fucose was detected in the supernatant of E. coli BL21 (DE3) lacZ Gal⁺ araA ΔwcaJ ΔfucI ΔfucK::($P_{tet}$-lacY)(cscBKAR)($P_{tet}$-wgbLco-neo)($P_{tet}$-manCB-$P_{T5}$-gmd, wcaG-dhfr)($P_{tet}$-afcAco-tet) grown on sucrose, and glycerol, respectively, using lactulose as acceptor, as shown by TCL (FIG. 3) and HPLC (FIGS. 4 and 5).

Figure 3:
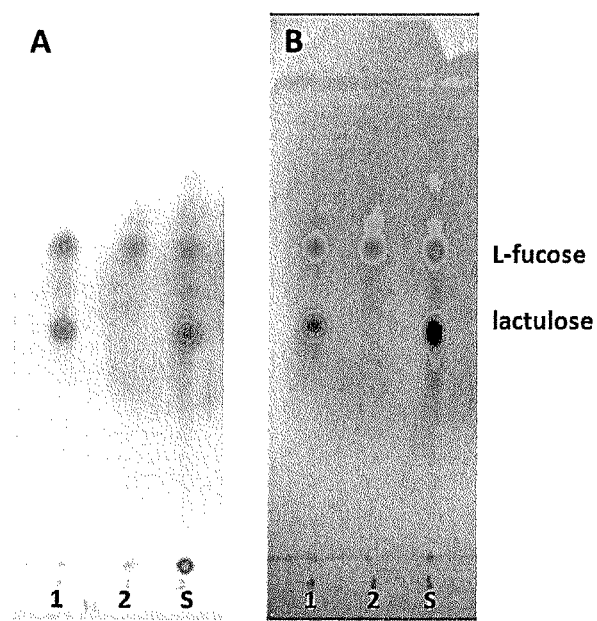
FIG. 3 a chromatogram (thin layer chromatography) showing the presence of exemplary embodiment L-fucose in the supernatant of microorganisms according to the invention, grown on sucrose (A) or glycerol (B)

FIG. 3 shows the results of the thin layer chromatography (TLC) for the microorganism grown on glycerol (A) or grown on sucrose (B) in the presence of acceptor-substrate lactulose: Lane 1 (both, FIGS. 3A and 3B): In the supernatant of E. coli BL21 (DE3) lacZ Gal⁺ araA ΔwcaJ ΔfucI ΔfucK::($P_{tet}$-lacY)(cscBKAR)($P_{tet}$-wgbLco-neo)($P_{tet}$-manCB-$P_{T5}$-gmd, wcaG-dhfr)($P_{tet}$-afcAco-tet) L-fucose was detected by TCL as verified with authentic reference substances (S: L-fucose (Glycom, Denmark), lactulose (Sigma, Germany).

Lane 2 (both, FIG. 3A and FIG. 3B): Lactulose was hydrolyzed enzymatically and the resulting monosaccharides were degraded by strain E. coli BL21 (DE3) lacZ Gal⁺ araA ΔwcaJ ΔfucI ΔfucK::($P_{tet}$-lacY)(cscBKAR)($P_{tet}$-wgbLco-neo)($P_{tet}$-manCB-$P_{T5}$-gmd, wcaG-dhfr)($P_{tet}$-afcAco-tet) at 37° C.

Figure 4A:
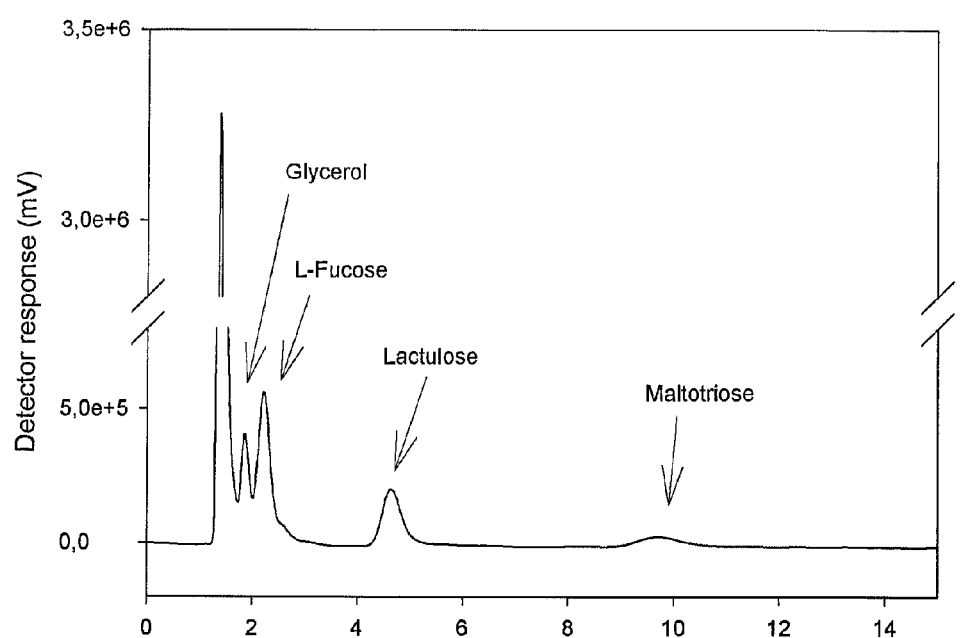
FIGS. 4A-4B HPLC chromatograms showing the production of L-fucose by the recombinant microorganism according to the invention grown on glycerol (A) or sucrose (B). Peaks with retention times 2.2 minutes, 4.6 minutes, and 9.8 minutes correspond to L-fucose, lactulose and maltotriose (internal standard), respectively.

FIG. 4 shows the fucose production by E. coli BL21 (DE3) lacZ Gal⁺ araA ΔwcaJ ΔfucI ΔfucK::($P_{tet}$-lacY)(cscBKAR)($P_{tet}$-wgbLco-neo)($P_{tet}$-manCB-$P_{T5}$-gmd, wcaG-dhfr)($P_{tet}$-afcAco-tet) as determined by HPLC, wherein in FIG. 4A the supernatant of E. coli BL21 (DE3) lacZ Gal⁺ araA ΔwcaJ ΔfucI ΔfucK::($P_{tet}$-lacY)(cscBKAR)($P_{tet}$-wgbLco-neo)($P_{tet}$-manCB-$P_{T5}$-gmd, wcaG-dhfr)($P_{tet}$-afcAco-tet) grown on glycerol is shown; sample was taken at 64 h post fermentation start. Peaks with retention times of 1.9, 2.1, 4.6, and 9.8 minutes correspond to glycerol, L-fucose, lactulose, and maltotriose (internal standard), respectively. The HPLC measurement method is described above.

Figure 4B:
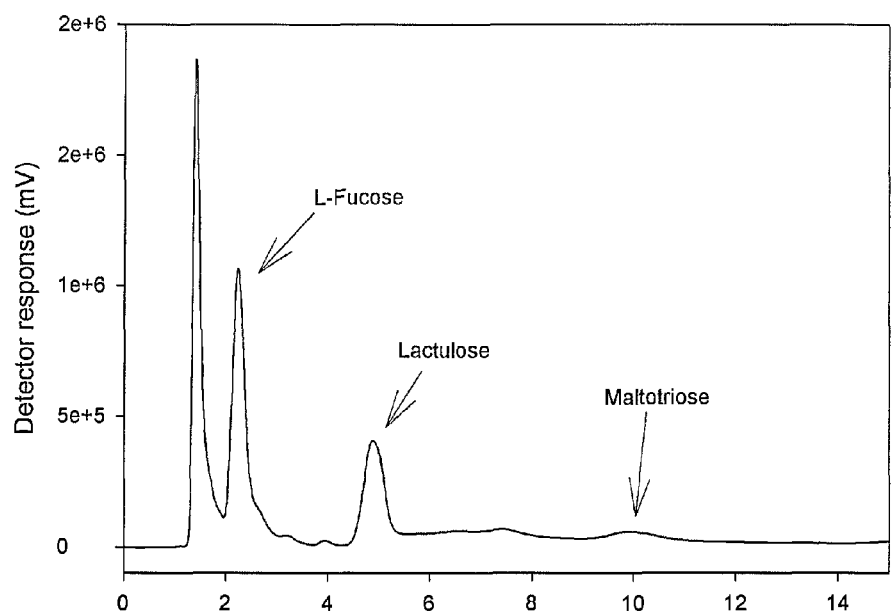

In FIG. 4B, the results of the HPLC analysis for the supernatant of E. coli BL21 (DE3) lacZ Gal⁺ araA ΔwcaJ ΔfucI ΔfucK::($P_{tet}$-lacY)(cscBKAR)($P_{tet}$-wgbLco-neo)($P_{tet}$-manCB-$P_{T5}$-gmd, wcaG-dhfr)($P_{tet}$-afcAco-tet) grown on sucrose is shown; sample was were taken at 66.3 h post fermentation start. Peaks with retention times of 2.2, 4.6, and 9.8 minutes correspond to L-fucose, lactulose, and maltotriose (internal standard), respectively. The HPLC measurement method id described above.

Hydrolyses of lactulose by beta-galactosidase and degradation of monosaccharides by strain E. coli BL21 (DE3) lacZ Gal⁺ araA ΔwcaJ ΔfucI ΔfucK::($P_{tet}$-lacY)(cscBKAR)($P_{tet}$-wgbLco-neo)($P_{tet}$-manCB-$P_{T5}$-gmd, wcaG-dhfr)($P_{tet}$-afcAco-tet)

Steril supernatant from the L-fucose producing cultures of strain E. coli BL21 (DE3) lacZ Gal⁺ araA ΔfucI ΔfucK ΔnagB ΔnagA::($P_{tet}$-lacY)(cscBKAR)($P_{tet}$-wgbLco-neo)($P_{tet}$-manCB-$P_{T5}$-gmd, wcaG-dhfr)($P_{tet}$-afcAco-tet) grown with sucrose, and glycerol, respectively, were obtained by centrifugation and filtration (0.22 µm pore size). The supernatants were diluted 1:10 in fresh mineral salts medium. Beta-galactosidase (purchased from Sigma Aldrich) was added to a concentration of 10 units mL⁻¹ and hydrolysis was performed at 37° C. for 3 h. Strain E. coli BL21 (DE3) lacZ Gal⁺ araA ΔwcaJ ΔfucI ΔfucK::($P_{tet}$-lacY)(cscBKAR)($P_{tet}$-wgbLco-neo)($P_{tet}$-manCB-$P_{T5}$-gmd, wcaG-dhfr)($P_{tet}$-afcAco-tet) was grown in 2YT rich medium containing the respective antibiotics at 37° C. to an OD660 nm of about 5. Cells of 10 mL culture were harvested under sterile conditions by centrifugation and resuspended in 2 mL of the β-galactosidase containing supernatant. Living cells degraded the monosaccharides resulting from the enzymatic hydrolysis in 16 h at 37° C.

Figure 5A:
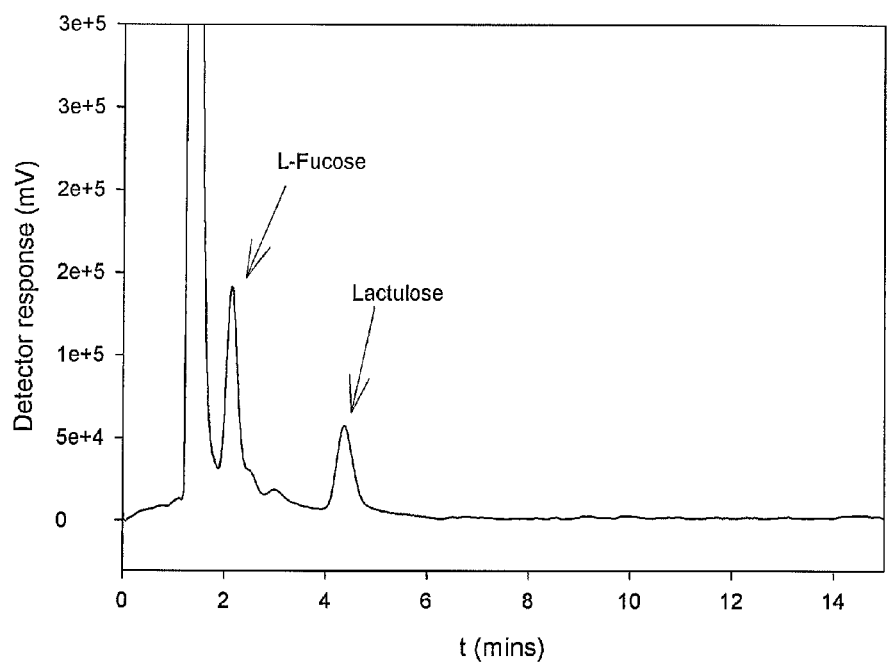
FIGS. 5A-5B HPLC chromatograms showing the effect of addition of beta-galactosidase to the fermentation medium, with FIG. 5A showing the HPLC chromatogram of fermentation medium prior beta-galactosidase addition, and with FIG. 5B showing the HPLC chromatogram post beta-galactosidase addition.
Figure 5B:
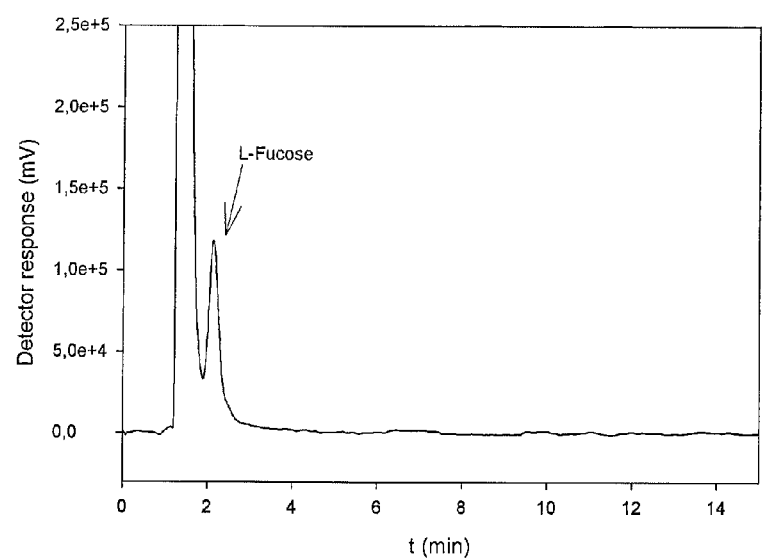

FIG. 5 shows the HPLC analysis of the in vitro enzymatic hydrolysis of lactulose and degradation of the monosaccharides by E. coli BL21 (DE3) lacZ Gal⁺ araA ΔwcaJ ΔfucI ΔfucK::($P_{tet}$-lacY)(cscBKAR)($P_{tet}$-wgbLco-neo)($P_{tet}$-manCB-$P_{T5}$-gmd, wcaG-dhfr)($P_{tet}$-afcAco-tet), wherein FIG. 5A shows the results with the supernatant of the sucrose grown culture (harvested at 66.3 h); before the β-galactosidase was added and after treatment with beta-galactosidase and degradation FIG. 5B. Peaks with retention times of 2.1, and 4.4 minutes correspond to L-fucose and lactulose, respectively.

Figure 6:
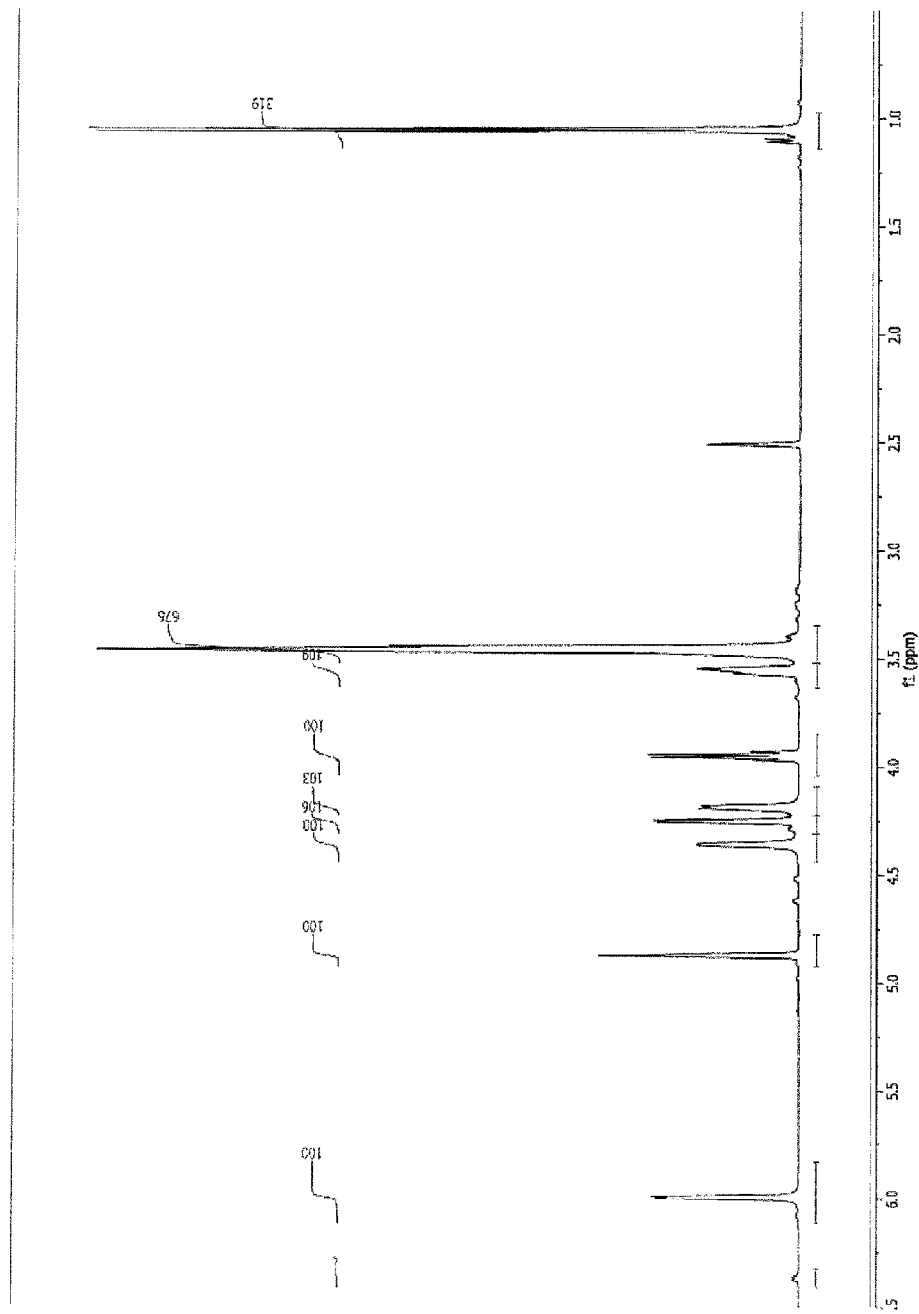

FIG. 6 shows the 1-H NMR spectrum of the purified L-fucose obtained by microbial fermentation. For the measurement 20 mg of substance were dissolved in 0.7 ml deuterated DMSO.

The presented results show that with the exemplary microorganism strain the exemplary monosaccharide L-fucose can be efficiently produced in free form in a large scale.

What is claimed is:

1. A process for producing L-fucose in free form using a bacterial microorganism, the process comprising the steps of:

a) providing a recombinant bacterial microorganism that has been transformed to contain a nucleic acid sequence encoding a bacterial alpha-1,2-fucosyltransferase specifically able to transfer fucose from an activated nucleotide fucose to lactose to form a lactose-fucose substrate, or to lactulose to form a lactulose-fuscose substrate, and a nucleic acid sequence encoding a bacterial 1,2-alpha-fucosidase not naturally occurring in the recombinant bacterial microorganism, the bacterial 1,2-alpha-fucosidase able to release the L-fucose from the lactose-fucose substrate or from the lactulose-fucose substrate, wherein the recombinant bacterial microorganism lacks a beta-galactosidase gene or comprises a deregulated beta-galactosidase-encoding gene, and wherein the recombinant bacterial microorganism is unable to metabolize L-fucose;

b) cultivating the recombinant bacterial microorganism in a medium suitable for growing the recombinant bacterial microorganism, whereby L-fucose is produced in a free form; and c) recovering the L-fucose from the medium.

2. The process of claim 1, wherein the medium comprises a carbon source, and wherein the carbon source is glycerol, sucrose, molasses, xylose, cellulose, or syngas.

3. The process of claim 1, wherein cultivating the recombinant bacterial microorganism is a batch or a continuous process.

4. The process of claim 1, wherein recovering free L-fucose from the medium comprises centrifuging the cultivated recombinant bacterial microorganism to obtain a supernatant and a recombinant bacterial microorganism pellet, and recovering the free L-fucose from the supernatant.

5. A process for producing L-fucose in free form using a bacterial microorganism, the process comprising the steps of:

a) providing a recombinant *E. coli* host cell that has been transformed to contain i) a wbgL gene encoding a bacterial alpha 1,2-fucosyltransferase, wherein the alpha 1,2-fucosyltransferase can transfer the fucose from an activated nucleotide fucose to lactose or lactulose to form a lactose-fucose-substrate or a lactulose-fucose-substrate, and ii) an afcA gene encoding a 1,2-alpha-fucosidase not naturally occurring in the recombinant *E. coli* host cell, wherein the 1,2-alpha-fucosidase can release L-fucose from the lactose-fucose-substrate or the lactulose-fucose-substrate; wherein the recombinant *E. coli* host cell is unable to metabolize the L-fucose;

b) cultivating the recombinant *E. coli* host cell in a medium suitable for growing the recombinant *E. coli* host cell, whereby L-fucose is produced in a free form; and c) recovering the L-fucose from the medium.

6. The process of claim 5, wherein the recombinant *E. coli* host cell is further transformed to contain the gal-operon (galETKM) genes and the lactose transporter gene lacY.

7. The process of claim 6, wherein the medium comprises a carbon source, and wherein the carbon source is glycerol, sucrose, molasses, xylose, cellulose, or syngas.

8. The process of claim 6, wherein cultivating the recombinant *E. coli* is a batch or a continuous process.

9. The process of claim 6, wherein recovering free L-fucose from the medium comprises centrifuging the cultivated *E. coli* host cell to obtain a supernatant and a *E. coli* host cell pellet, and recovering the free L-fucose from the supernatant.

10. The process of claim 1, wherein the recombinant bacterial microorganism is a recombinant *Escherichia coli*.

11. The process of claim 1, wherein the alpha-1,2-fucosyltransferase is encoded by a wbgL gene of *E. coli*.

12. The process of claim 1, wherein the 1,2-alpha-glycosidase is encoded by an afcA gene of *Bifidobacterium bifidum*.

* * * * *

SEQUENCE LISTING

<160> NUMBER OF SEQ ID NOS: 4

<210> SEQ ID NO 1
<211> LENGTH: 35
<212> TYPE: DNA
<213> ORGANISM: Artificial
<220> FEATURE:
<223> OTHER INFORMATION: Primer

<400> SEQUENCE: 1
ttactcagca ataaactgat attccgtcag gctgg                           35

<210> SEQ ID NO 2
<211> LENGTH: 86
<212> TYPE: DNA
<213> ORGANISM: Artificial
<220> FEATURE:
<223> OTHER INFORMATION: Primer

<400> SEQUENCE: 2
ttgataatct cgcgctcttc agcagtcaga ctttccatat agagcgtaat ttccgttaac    60
gtcggtagtg ctgaccttgc cggagg                                        86

<210> SEQ ID NO 3
<211> LENGTH: 58
<212> TYPE: DNA
<213> ORGANISM: Artificial
<220> FEATURE:
<223> OTHER INFORMATION: Primer

<400> SEQUENCE: 3
ctgtctctta tacacatctc ctgaaattgg ccagatgatt aattcctaat ttttgttg    58

<210> SEQ ID NO 4
<211> LENGTH: 50
<212> TYPE: DNA
<213> ORGANISM: Artificial
<220> FEATURE:
<223> OTHER INFORMATION: Primer

<400> SEQUENCE: 4
ctgtctctta tacacatctc agcattacac gtcttgagcg attgtgtagg            50